(12) United States Patent
Gulanes et al.

(10) Patent No.: US 10,920,924 B2
(45) Date of Patent: Feb. 16, 2021

(54) SLIDING BRACKET

(71) Applicant: Fisher & Paykel Healthcare Limited, Auckland (NZ)

(72) Inventors: Allen Brian Hautea Gulanes, Auckland (NZ); Shorojeet Dasgupta, Auckland (NZ); Jonathan Stuart McFedries, Auckland (NZ); Stephen Watts, Auckland (NZ); Lucila San Jose De Jesus, Auckland (NZ); James Alexander Gordon, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 1068 days.

(21) Appl. No.: 15/325,873

(22) PCT Filed: Jul. 15, 2015

(86) PCT No.: PCT/NZ2015/050091
§ 371 (c)(1),
(2) Date: Jan. 12, 2017

(87) PCT Pub. No.: WO2016/010438
PCT Pub. Date: Jan. 21, 2016

(65) Prior Publication Data
US 2017/0152989 A1   Jun. 1, 2017

Related U.S. Application Data

(60) Provisional application No. 62/024,598, filed on Jul. 15, 2014, provisional application No. 62/075,695, filed on Nov. 5, 2014.

(51) Int. Cl.
*F16L 3/01* (2006.01)
*F16L 3/015* (2006.01)
(Continued)

(52) U.S. Cl.
CPC ........ *F16M 13/022* (2013.01); *A61M 16/109* (2014.02); *A61M 16/16* (2013.01);
(Continued)

(58) Field of Classification Search
CPC .. F16M 13/022; F16M 11/041; F16M 11/048; A61M 16/109; A61M 16/16;
(Continued)

(56) References Cited

U.S. PATENT DOCUMENTS 4,141,542 A * 2/1979 Wolff .................... B25B 5/101
                                                    269/155
5,775,395 A * 7/1998 Wilkins ................ B25B 11/005
                                                    144/135.2

(Continued)

OTHER PUBLICATIONS

Nov. 13, 2015, International Search Report for PCT Application No. PCT/NZ2015/050091 filed on Jul. 15, 2015.

*Primary Examiner* — Nkeisha Smith
(74) *Attorney, Agent, or Firm* — Knobbe, Martens, Olson & Bear LLP

(57) ABSTRACT

A bracket for extensibly mounting a medical or surgical apparatus, and more particularly a humidification apparatus, to a support structure. The bracket comprises a base member securable to the support structure, a mounting member to which the humidification apparatus may be secured, and an extension mechanism moveably engaging the base member (Continued)

and the mounting member. The mounting member is reversibly extensible from a retracted position substantially proximate the base member to an extended position projecting beyond the base member. Also disclosed are a humidification apparatus and a support stand each comprising the extensible bracket.

17 Claims, 8 Drawing Sheets

(51) Int. Cl.
| | |
|---|---|
| *F16M 13/02* | (2006.01) |
| *A61M 16/16* | (2006.01) |
| *A61M 16/10* | (2006.01) |
| *F16M 11/04* | (2006.01) |
| *F16B 2/06* | (2006.01) |
| *F16L 3/12* | (2006.01) |

(52) U.S. Cl.
CPC ............... *F16B 2/065* (2013.01); *F16L 3/01* (2013.01); *F16L 3/015* (2013.01); *F16L 3/1226* (2013.01); *F16M 11/041* (2013.01); *F16M 11/048* (2013.01); *F16M 13/02* (2013.01); *A61M 2209/082* (2013.01)

(58) Field of Classification Search
CPC ..... A61M 2209/082; F16B 2/065; F16L 3/01; F16L 3/015; F16L 3/1226
USPC ............................................. 144/286.5, 287
See application file for complete search history.

(56) References Cited

U.S. PATENT DOCUMENTS

| | | | | |
|---|---|---|---|---|
| 6,619,348 | B2 * | 9/2003 | Wang ................... | B23D 47/025 108/143 |
| 6,745,803 | B2 * | 6/2004 | Sanfilippo ............ | B23D 47/025 144/286.5 |
| 7,490,643 | B2 * | 2/2009 | Liu ....................... | B23D 47/025 108/143 |
| 7,677,283 | B2 * | 3/2010 | Hooker ................ | B25H 1/0021 144/286.5 |
| 10,517,397 | B2 * | 12/2019 | Min ..................... | A47B 88/477 |
| 10,588,410 | B2 * | 3/2020 | Miles .................. | A47B 88/57 |
| 2005/0161113 | A1 * | 7/2005 | Chiu .................... | B25H 1/0078 144/134.1 |
| 2007/0084526 | A1 * | 4/2007 | Radermacher ........... | B27C 5/02 144/286.1 |
| 2011/0079685 | A1 * | 4/2011 | Kwak ................... | F16M 11/105 248/65 |
| 2013/0193824 | A1 * | 8/2013 | Koenig ................. | A47B 88/437 312/334.11 |
| 2015/0238377 | A1 * | 8/2015 | Muhammad ............. | F16L 3/24 248/68.1 |

* cited by examiner

SLIDING BRACKET

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to a bracket for moveably mounting a medical or surgical apparatus to a supporting structure. More particularly, though not exclusively, the present disclosure relates to a bracket providing slidable mounting between a humidification apparatus and a supporting structure.

Description of the Related Art

Humidification systems are increasingly used in respiratory support and surgical procedures to humidify breathing or insufflation gases with water vapour to reduce the risk of dehydration or dessication and the effects of evaporative cooling.

Surgical humidification systems, for example, generally comprise a source of pressurised (with respect to atmospheric pressure) insufflation gases, a surgical humidification apparatus in fluid communication with the pressurised insufflation gases source to heat and/or humidify the insufflation gases before delivery to a patient, a conduit in fluid communication with the humidification apparatus to convey the insufflation gases towards the patient, and a patient interface (such as a laparoscope) in fluid communication with the conduit to deliver the humidified insufflation gases to the patient's abdominal cavity. An example of such a surgical humidification system is the HumiGard™ system, available from Fisher & Paykel Healthcare Ltd. of Auckland, New Zealand.

Respiratory humidification systems similarly comprise a source of pressurised breathing gases, a humidification apparatus in fluid communication with the pressurised breathing gases, a conduit in fluid communication with the humidification apparatus, and a patient interface (such as a face mask, nasal mask, or nasal cannula) in fluid communication with the conduit to supply the humidified breathing gases to the patient when fitted. A humidifier comprises, for example, a humidification chamber adapted to contain a volume of water in thermal contact with a heater plate that is part of and is controlled by a base unit. Breathing gases are received from the pressurised breathing gases source at an inlet to the chamber, and supplied to the patient by way of the conduit in fluid communication with an outlet of the chamber. In use, the breathing gases received at the inlet flow to the outlet across the surface of the contained water, through the ullage or headspace in the chamber. The water is heated by the controlled heater plate which in turn heats and humidifies the gases delivered to the patient. The pressurised gases source may comprise a flow generator such as an integral blower, or a separate gases source in fluid communication with the inlet via a conduit. Such respiratory humidification systems are in widespread use in both hospital and home care environments.

The humidification apparatus of such humidification systems generally needs to be provided conveniently proximate to at least some of the other components of the system. Previously, the humidification apparatus has merely been provided on a shelf of an instrument stand, which is commonly in the form of a mobile wheeled cart. However, there is a risk that the humidification apparatus may be knocked or pulled off the shelf, in particular due to forces which may be inadvertently exerted upon the conduits and/or power cables. This presents a safety hazard in view of the heater plate which may become exposed and water which may spill from the apparatus. Furthermore, additional shelving or the outer structure of the instrument stand above and/or beside the humidification apparatus may impede access to the apparatus, in particular for the attachment of conduits which may project upwardly from the humidification chamber, for example. Accordingly, the humidification apparatus is commonly semi-permanently or permanently attached to the shelf in a position projecting from the instrument stand. As a result, the humidification apparatus may obstruct medical or surgical personnel, prevent closure of the instrument stand doors, be knocked or damaged as the instrument stand is moved, or otherwise create a nuisance which is especially inconvenient when use of the apparatus is not immediately required.

BRIEF SUMMARY

It is an object of the present disclosure to provide a bracket which overcomes or at least ameliorates one or more disadvantages of the prior art, or alternatively to at least provide the public with a useful choice.

Further objects of the present disclosure will become apparent from the following description.

According to at least one aspect of the present disclosure, a bracket for extensibly mounting a medical apparatus to a support structure can have one, some, or all of the following features, as well as other features described herein. The bracket comprises a base member securable to the support structure, a mounting member to which the medical apparatus may be secured, and an extension mechanism moveably engaging the base member and the mounting member. The mounting member is reversibly extensible from a retracted position substantially proximate the base member to an extended position projecting beyond the base member. The medical apparatus may be a humidification apparatus, an insufflation apparatus, or another suitable type of medical apparatus. The support structure may be an instrument stand, a tower, a cart, a videocart, or another suitable type of support structure.

The mounting member may be slidable with respect to the base member. The extension mechanism may comprise a pair of rails. The extension mechanism may comprise a pair of carriages slidably engaged with the pair of rails. The pair of rails may be attached to or integral with the base member. The pair of carriages may be attached to or integral with the mounting member at or adjacent a rearward end of the mounting member, whereby a forward end of the mounting member may project beyond the base member in the extended position. The pair of rails may define a substantially linear range of movement in opposing directions between the retracted position and the extended position. The forward end of the mounting member may be substantially vertically coincident with a forward end of the base member in the retracted position. Each one of the pair of carriages may comprise a channel slidably receiving and retaining a respective one of the pair of rails. The pair of rails may extend linearly from, at, or adjacent a rearward end of the base member to, at, or adjacent a forward end of the base member. The extension mechanism may comprise additional carriages. The extension mechanism may comprise additional rails. Two or more carriages may be slidably engaged with each rail.

The bracket may comprise a cable guide for receiving a power cable of the medical apparatus and directing the power cable away from the extension mechanism. The cable guide may comprise an annular cable guide on each of the mounting member and the base member. The annular cable guides may be adapted to direct the power cable substantially upwardly away from the bracket to prevent obstruction of the extension mechanism as the mounting member is retracted in use. The cable guide may comprise an elongate cable guide attached at opposing ends to the mounting member and the base member and engageable with substantially the entire length of the power cable therebetween. The elongate cable guide may be adapted to secure a length of the power cable sufficient to allow extension of the bracket. The elongate cable guide may be adapted to direct the power cable substantially upwardly away from the bracket to prevent obstruction of the extension mechanism as the mounting member is retracted in use. The bracket may comprise a front stopper to limit movement of the mounting member in a first direction past the extended position. The bracket may comprise a back stopper to limit movement of the mounting member in a second direction past the retracted position. The bracket may comprise a lanyard attached at one end to the bracket and attachable at the other end to a cable of the medical apparatus to prevent loss of the cable.

The bracket may be selectively engageable with any one of a plurality of mounting adapters for securing the bracket, and more particularly the base member, to the support structure. Each of the plurality of mounting adapters may differ in at least one aspect. The base member may comprise a plurality of mounting holes enabling engagement with each of the plurality of mounting adapters. The plurality of mounting adapters may comprise at least a first mounting adapter for securing the bracket to a substantially vertical surface. The plurality of mounting adapters may comprise at least a second mounting adapter for securing the bracket to a substantially horizontal surface. The first mounting adapter may comprise a substantially L-shaped side-mounting adapter for securing the bracket to a side wall, such as a side wall of the support structure. The second mounting adapter may comprise a clamp for securing the bracket to a shelf, such as a shelf of the support structure. The bracket may comprise a clamp for securing the bracket to the support structure.

The clamp may comprise a C-clamp, a spring clamp, a speed clamp, or another suitable type of clamp. The clamp may comprise a jaw projecting downwardly and rearwardly from a forward end of the base member. The clamp may comprise a screw extending through a threaded aperture in the jaw. Rotation of the screw may cause axial movement of the screw to respectively engage or release a portion of the support structure received between the base member and the jaw. The jaw may be either attached to or integral with the base member. The rearwardly-projecting portion of the jaw may be elastically deformable to prevent plastic deformation of the clamp. The bracket may comprise at least one of the plurality of mounting adapters. For example, the bracket and at least one of the mounting adapters may be supplied together as a kit of parts.

The base member may comprise a base plate. The mounting member may comprise a mounting plate. The mounting member may comprise an upright support member. The upright support member may be adapted to engage a rear surface of the medical apparatus. The mounting member and the upright support member may be unitary and stamped from a single sheet of metal. The upright support member may comprise a channel for slidably receiving the medical apparatus in a substantially vertical direction. The channel may be attached to the upright support member using bolts that pass through apertures in the channel and the upright support member. The upright support member may comprise multiple sets of apertures whereby the channel may be attached to an upper attachment position of the upright support member or a lower attachment position of the upright support member. The upper and lower attachment positions may be suitable for use with different types or sizes of the medical apparatus. The channel may be adapted for securing the medical apparatus against movement in a transverse direction. The medical apparatus may comprise a complementary adapter attached to or integral with the medical apparatus. The complementary adapter may comprise a projection to engage the channel. The base member may comprise one or more gripping feet on a lower surface to engage the support structure. The mounting member may comprise a handle at a forward end of the mounting member to facilitate extension and retraction of the mounting member.

According to at least one aspect of the present disclosure, a bracket for slidably mounting a medical apparatus to a support structure can have one, some, or all of the following features, as well as other features described herein. The bracket comprises a base plate and a mounting plate. The base plate comprises a first side engageable and securable to the support structure. The base plate comprises an opposing second side comprising a pair of rails. The mounting plate comprises a first side comprising a pair of carriages slidably engaging the pair of rails. The mounting plate comprises a second side adapted to support the medical apparatus. The mounting plate is slidable in opposing linear directions along the rails to linearly extend and retract the medical apparatus with respect to the base plate and the support structure. The medical apparatus may be a humidification apparatus, an insufflation apparatus, or another suitable type of medical apparatus. The support structure may be an instrument stand, a tower, a cart, a videocart, or another suitable type of support structure.

The pair of rails may extend linearly from, at, or adjacent a rearward end of the base plate to, at, or adjacent a forward end of the base plate. The bracket may comprise a cable guide for receiving a power cable of the medical apparatus and directing the power cable away from the pair of rails and the pair of carriages. The cable guide may comprise an annular cable guide on each of the mounting plate and base plate. The annular cable guides may be adapted to direct the power cable substantially upwardly away from the bracket to prevent obstruction of the mounting plate as the mounting plate is retracted in use. The cable guide may comprise an elongate cable guide attached at opposing ends to the mounting plate and the base plate and engageable with substantially the entire length of the power cable therebetween. The elongate cable guide may be adapted to secure a length of the power cable sufficient to allow extension of the bracket. The elongate cable guide may be adapted to direct the power cable substantially upwardly away from the bracket to prevent obstruction of the mounting plate as the mounting plate is retracted in use. The bracket may comprise a lanyard attached at one end to the bracket and attachable at the other end to a cable of the medical apparatus to prevent loss of the cable.

The bracket may be selectively engageable with any one of a plurality of mounting adapters for securing the bracket, and more particularly the base plate, to the support structure. Each of the plurality of mounting adapters may differ in at least one aspect. The base member may comprise a plurality of mounting holes enabling engagement with each of the plurality of mounting adapters. The plurality of mounting adapters may comprise at least a first mounting adapter for securing the bracket to a substantially vertical surface. The plurality of mounting adapters may comprise at least a second mounting adapter for securing the bracket to a substantially horizontal surface. The first mounting adapter may comprise a substantially L-shaped side-mounting adapter for securing the bracket to a side wall, such as a side wall of the support structure. The second mounting adapter may comprise a clamp for securing the bracket to a shelf, such as a shelf of the support structure. The bracket may comprise a clamp for securing the bracket to the support structure.

The clamp may comprise a C-clamp, a spring clamp, a speed clamp, or another suitable type of clamp. The clamp may comprise a jaw projecting downwardly and rearwardly from a forward end of the base plate. The clamp may comprise a screw extending through a threaded aperture in the jaw. Rotation of the screw may cause axial movement of the screw to respectively engage or release a portion of the support structure received between the base plate and jaw. The jaw may be either attached to or integral with the base plate. The rearwardly-projecting portion of the jaw may be elastically deformable to prevent plastic deformation of the clamp. The bracket may comprise at least one of the plurality of mounting adapters. For example, the bracket and at least one of the mounting adapters may be supplied together as a kit of parts.

The mounting plate may comprise an upright support member. The upright support member may be adapted to engage a rear surface of the medical apparatus. The mounting plate and the upright support member may be unitary and stamped from a single sheet of steel. The upright support member may comprise a channel for slidably receiving the medical apparatus in a substantially vertical direction. The channel may be adapted for securing the medical apparatus against movement in a transverse direction. The medical apparatus may comprise a complementary adapter attached to or integral with the medical apparatus. The complementary adapter may comprise a projection to engage the channel. The base plate may comprise one or more gripping feet on a lower surface to engage the support structure. The mounting plate may comprise an upwardly-projecting handle to facilitate extension and retraction of the mounting plate.

According to at least one aspect of the present disclosure, a humidification apparatus can have one, some, or all of the following features, as well as other features described herein. The humidification apparatus comprises a humidification chamber for containing a volume of water. The humidification chamber comprises an inlet for receiving gases from a gases source. The humidification chamber comprises an outlet for supplying humidified gases to a patient. The humidification apparatus comprises a heater plate thermally coupled with the humidification chamber to heat the water and humidify gases received from the gases source. The humidification apparatus comprises a controller adapted to control the heater plate and the temperature and/or humidity of the humidified gases. The humidification apparatus comprises a bracket for slidably mounting the humidification apparatus to a substantially horizontal surface.

The substantially horizontal surface may comprise a shelf. The substantially horizontal surface may comprise a shelf of a support structure. The bracket may comprise a base member securable to the substantially horizontal surface. The bracket may comprise an extension mechanism slidably engaging the humidification apparatus with the base member. The humidification apparatus may be reversibly extensible from a retracted position substantially proximate the base member to an extended position projecting beyond the base member. The bracket may comprise a mounting member attached to or integral with the humidification apparatus and the extension mechanism. The mounting member may comprise an upright support member. The upright support member may be adapted to engage a rear surface of the humidification apparatus. The upright support member may comprise a channel for slidably receiving the humidification apparatus in a substantially vertical direction. The channel may be adapted for securing the humidification apparatus against movement in a transverse direction. The humidification apparatus may comprise an adapter attached to or integral with the humidification apparatus. The adapter may comprise a projection to engage the channel. The bracket may comprise at least one of a plurality of mounting adapters that may be selectively engageable with the bracket for mounting the bracket to the support structure. Each of the plurality of mounting adapters may differ in at least one aspect.

According to at least one aspect of the present disclosure, a support structure for medical equipment can have one, some, or all of the following features, as well as other features described herein. The support structure comprises an outer structure comprising at least bottom, top, and side walls, one or more shelves within the outer structure extending substantially horizontally between the side walls, and a bracket as previously described that is secured to the outer structure or the shelf of the support structure. The bracket is extensible from a retracted position substantially within the outer structure to an extended position projecting at least in part beyond the outer structure.

A humidification apparatus may be securable to the mounting portion of the bracket. The support structure may comprise the humidification apparatus. The support structure may comprise a power source. The support structure may comprise an isolating transformer. The support structure may comprise a residual current device. The support structure may comprise a plurality of caster wheels depending downwardly from the bottom wall.

In further aspects the disclosed apparatus and systems may broadly be said to comprise a humidification apparatus or an support structure comprising a bracket according to previously described aspects of the present disclosure.

For purposes of summarizing the disclosed apparatus and systems, certain aspects, advantages, and novel features of the disclosed apparatus and systems have been described herein. It is to be understood that not necessarily all such advantages may be achieved in accordance with any particular embodiment of the disclosed apparatus and systems. Thus, the disclosed apparatus and systems may be embodied or carried out in a manner that achieves or optimizes one advantage or group of advantages as taught herein without necessarily achieving other advantages as may be taught or suggested herein.

Yet further aspects of the disclosed apparatus and systems, which should be considered in all its novel aspects, will become apparent from the following description.

BRIEF DESCRIPTION OF DRAWINGS

These and other features, aspects, and advantages of the present disclosure will be described with respect to the following figures, which are intended to illustrate and not to limit the preferred embodiments.

DETAILED DESCRIPTION

Figure 1:
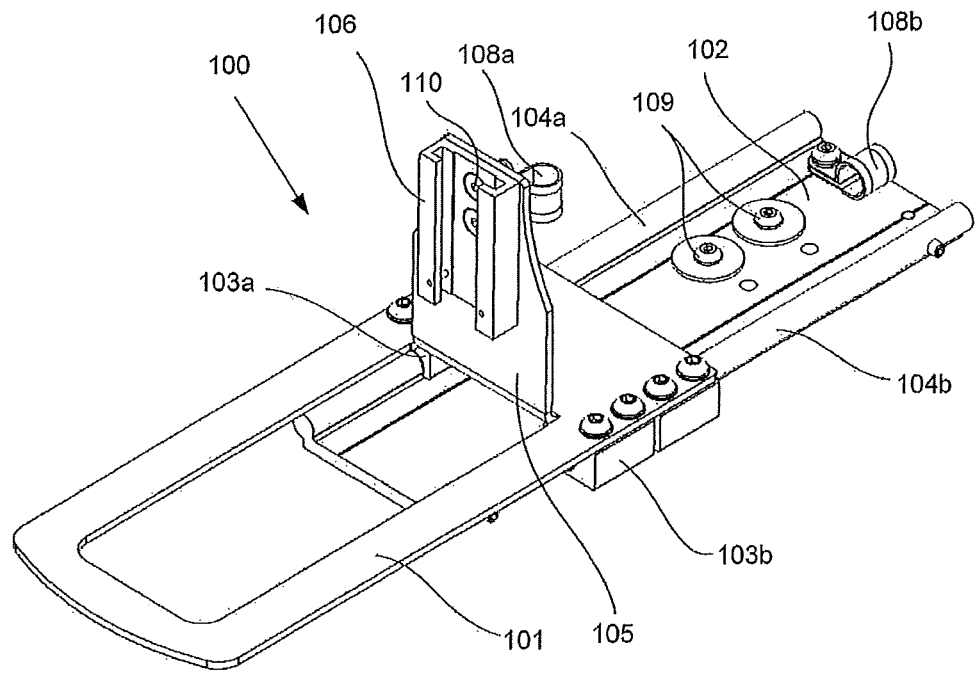
FIG. 1 shows an isometric view of a bracket according to an embodiment of the present disclosure and in an extended position.

Throughout the disclosure like reference numerals will be used to refer to like features in different embodiments. However, those features need not necessarily be identical in different embodiments of the bracket.

FIG. 1 shows an isometric view of a bracket 100 according to an embodiment of the present disclosure and in an extended position. The bracket 100 comprises an mounting member 101 slidably engaging a lower base member 102 by way of an extension mechanism, and more particularly a linear sliding mechanism. The sliding mechanism in this example comprises carriages 103a, 103b slidably engaging respective elongate rails 104a, 104b that may be attached to or, as illustrated in FIG. 1, integral with the lower base member 102. In some embodiments, the elongate rails 104a, 104b may have a substantially circular cross-section corresponding substantially with channels in the carriages 103a, 103b through which the elongate rails 104a, 104b may pass. The carriages 103a, 103b may comprise bearings to reduce friction between the carriages 103a, 103b and the rails 104a, 104b.

The mounting member 101 comprises an upstanding or upright support member 105, with a channel 106 adapted to slidably receive a humidification or other medical or surgical apparatus (not shown) in a substantially vertical direction as described in further detail below. In some embodiments, the channel 106 may be attached to the upright support member 105 by bolts 110 inserted through apertures (obscured) in the upright support member 105 and in the channel 106. In some embodiments, the channel 106 may be integral with the upright support member 105. In some embodiments, the upright support member 105 may be integral with the mounting member 101 as illustrated in FIG. 1, and in particular may be stamped from the same metal sheet as the mounting member 101. In some embodiments, the upright support member 105 and the mounting member 101 may comprise distinct components attached in any suitable manner.

Also shown in FIG. 1 are cable guides 108a, 108b respectively mounted to the mounting member 101, or more particularly to the upright support member 105 and the lower base member 102.

As used herein, the term "support structure" refers to a fixed or moveable structure, which may already be in use in operating theatres or hospital wards for other purposes, and in particular purposes coincident with the use of a humidification or other medical or surgical apparatus. A support structure may alternatively be referred to as an "instrument stand", "tower", "cart", or "videocart", and may house or store other surgical or medical equipment, such as an insufflator or medical imaging equipment for endoscopic surgery, for example. A support structure may also comprise any other similar structure comprising an outer structure or framework and internal shelving, for example. The bracket 100 may be secured atop any of the top or bottom wall or shelving of such a support structure. Other embodiments of the bracket 100 may alternatively be attached to a vertical surface, such as the internal or external surface of a side wall, for example. A support structure may be provided with caster wheels for easy movement of the support structure and equipment between and within operating theatres, for example. Alternatively, the bracket 100 may be mounted to furniture, for example a bedside table, or adapted for mounting to another vertical surface, such as a wall, without departing from the scope of the disclosure.

In use, the lower base member 102 may be secured to a shelf of a support structure by way of any suitable fastener, such as bolts 109 inserted through apertures in the base member 102. In some embodiments, the lower base member 102 is secured to the support structure by a clamp (not shown) which may be fitted from the front to minimise access difficulties in securing the bracket 100 to the support structure. In some embodiments, the clamp may be preferred if the bracket 100 needs to be removed frequently. The clamp may be separable from or integral with the lower base member 102.

Figure 2:
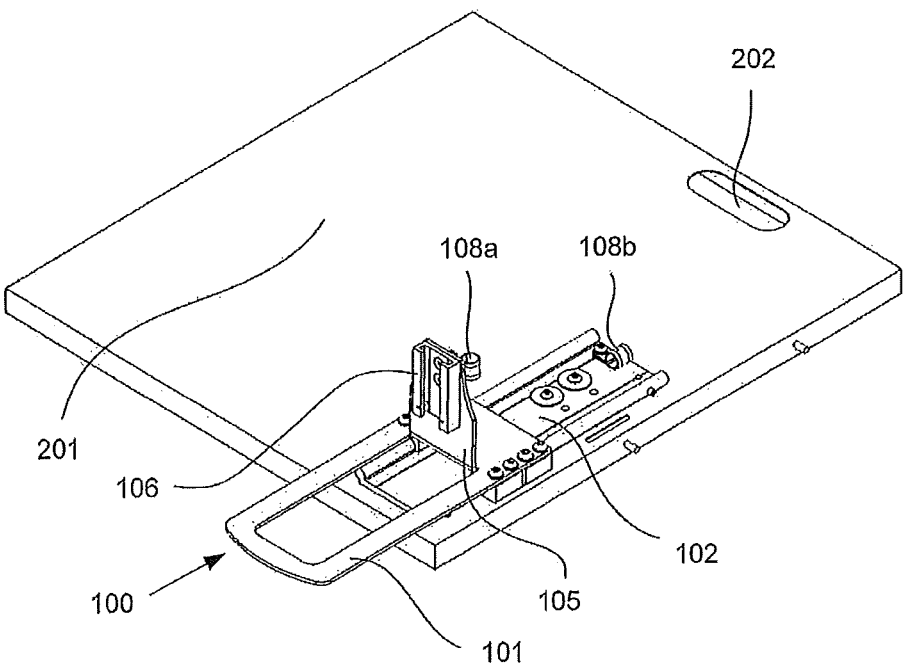
FIG. 2 shows an isometric view of the bracket of FIG. 1 attached to a shelf.

FIG. 2 shows an isometric view of the bracket 100, with the lower base member 102 of the bracket 100 secured to a shelf 201 of a support structure in such a way that the mounting member 101 and a humidification apparatus (not shown) thereupon may be extended to project at least in part beyond the shelf 201 to facilitate use and/or configuration of the humidification apparatus. Outer portions of the support structure are omitted from FIG. 2 for clarity. The humidification apparatus and the mounting member 101 can thus be retracted entirely within the support structure to protect the humidification apparatus and/or to avoid obstructing medical or surgical personnel.

The humidification apparatus is removably secured to the mounting member 101, and more particularly to the channel 106. In some embodiments, a complementary adapter may be attached to or integral with the humidification apparatus to slidably engage the channel 106 in a vertical direction and secure the humidification apparatus against movement in a transverse or non-vertical direction. The humidification apparatus may rest upon the mounting member 101. In some embodiments, any other permanent or temporary fastener may be used, including but not limited to one or more of adhesives, hook and loop fasteners, or clamps, for example.

In some embodiments, the support structure (not shown in its entirety in FIG. 2, but which comprises the shelf 201) may comprise a power source (not shown), for example but not limited to a power strip comprising a plurality of power outlets. In some embodiments, the power source comprises an isolating transformer. In some embodiments, the power source comprises a residual current device. A power cable for the humidification apparatus may pass through the cable guides 108a, 108b, ideally with sufficient excess of the power cable therebetween to ensure that the bracket 100 can fully extend, and then connect to the power source. The cable guides 108a, 108b urge excess of the power cable upwardly in such a way as to prevent the power cable obstructing or jamming the bracket 100 as the mounting member 101 is retracted. The shelf 201 may comprise an opening 202 through which the power cable may pass for connection to the power source which may be provided beneath the shelf 201.

Figure 3:
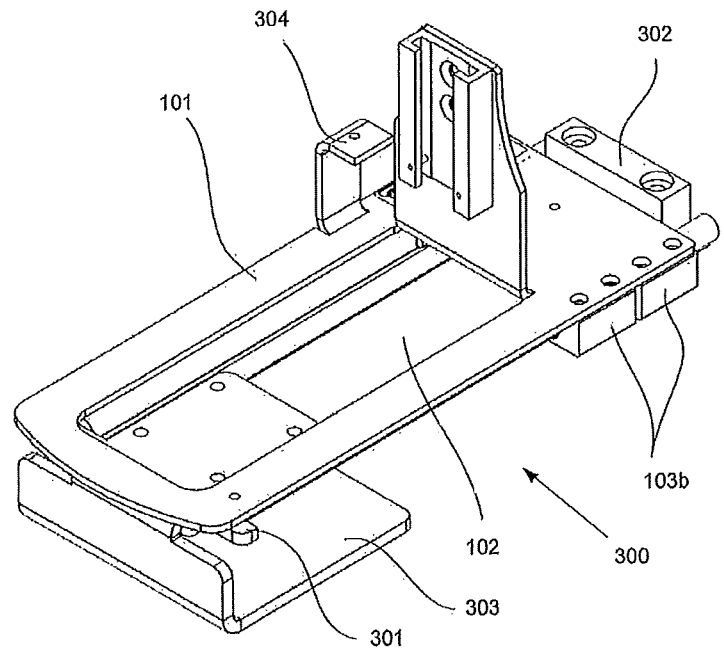
FIG. 3 shows an isometric view of a bracket according to an embodiment of the present disclosure and in a retracted position.
Figure 4:
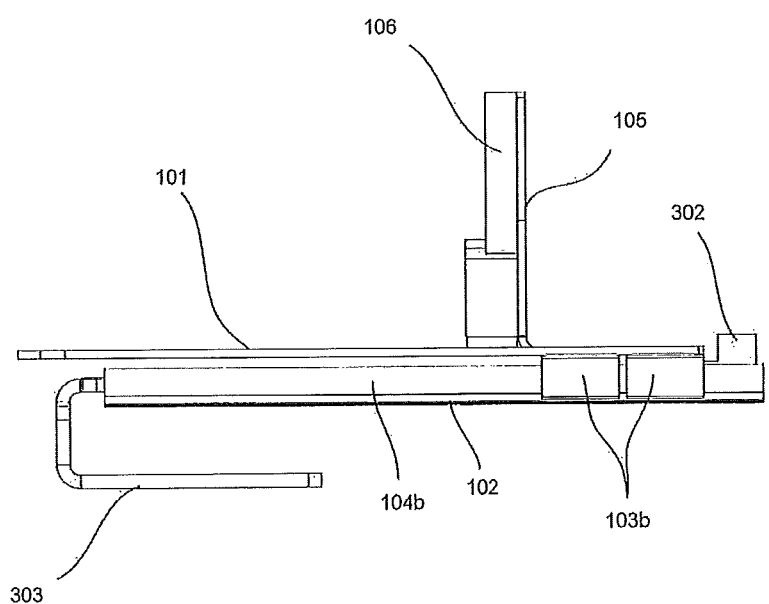
FIG. 4 shows a side view of the bracket of FIG. 3.

FIG. 3 shows an isometric view, and FIG. 4 a side view, of a bracket 300 according to an embodiment of the present disclosure and in a retracted position.

In some embodiments, the bracket 300 may comprise a front stopper 301 and a back stopper 302 to limit movement of the mounting member 101 therebetween and to avoid derailing of the carriages 103a (obscured), 103b. In some embodiments, either or both of the stoppers 301, 302 may be selectively removable so that the mounting member 101 (possibly with the humidification apparatus remaining secured thereto), may be removed from the lower base member 102 and the support structure for purposes of, for example, maintenance, replacement, or mating with another lower base member which may be secured to another support structure.

The bracket 300 also has a clamp comprising a jaw 303 projecting downwardly and rearwardly from a forward end of the lower base member 102 and within which a front edge of a shelf of the support structure (not shown) may be received. A threaded screw extending through a threaded aperture (not shown) in the jaw 303 may conveniently secure the bracket 300 to the support structure.

The bracket 300 comprises a cable holder 304 projecting upwardly from the mounting member 101 and adapted to receive and retain one end of a cable guide 605 as described in further detail below.

In FIG. 4, the carriage 103b comprises a pair of carriages that engage the elongate rail 104b, and the carriage 103a comprises a pair of carriages that engage the elongate rail 104a (obscured in FIG. 3). The carriages 103a, 103b are attached at or adjacent a rearward end of the mounting member 101, whereby forward movement of the carriages 103a, 103b towards the forward end of the lower base member 102 causes a forward end of the cantilevered mounting member 101 to extend beyond the lower base member 102, until a forward-most of each of the carriages 103a, 103b engages the front stopper 301.

Figure 5:
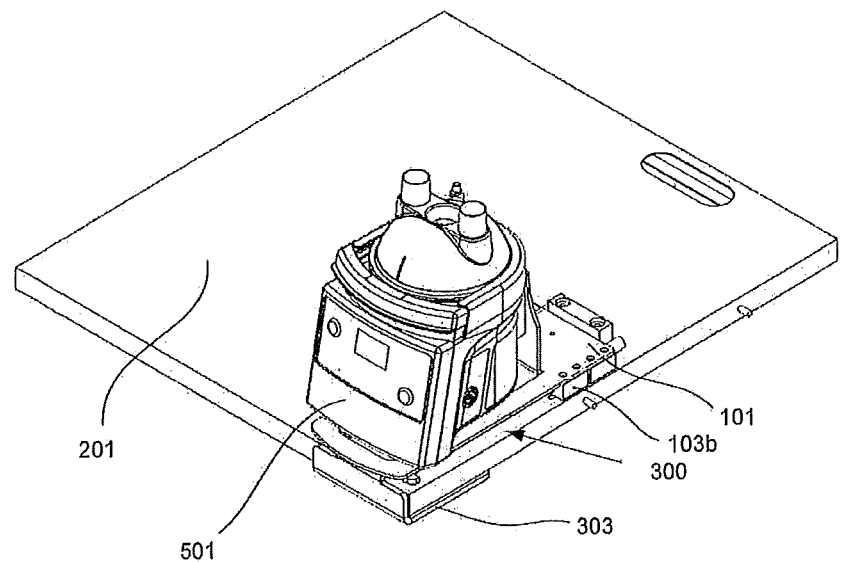
FIG. 5 shows an isometric view of the bracket of FIGS. 3 and 4 attached to a shelf and a humidification apparatus.

FIG. 5 shows an isometric view of the bracket 300 attached to the shelf 201 and with an example humidification apparatus 501 secured to the bracket 300. The humidification apparatus 501 may be retracted so that it does not project beyond a front edge of the shelf 201. The remainder of the support structure comprising the shelf 201, such as the outer structure and additional shelving, is again omitted for clarity, but the humidification apparatus 501 preferably may be retracted so that it also does not project beyond the front edge of such remainder of the support structure.

Figure 6:
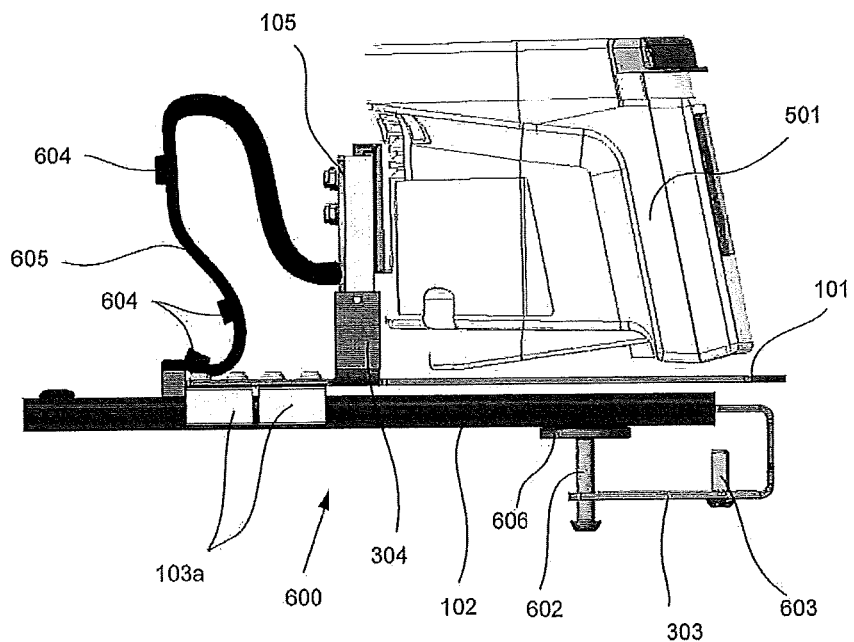
FIG. 6 shows a side view of a bracket according to an embodiment of the present disclosure and in a retracted position.

FIG. 6 shows a side view of a bracket 600 according to an embodiment of the present disclosure and in a retracted position. In this embodiment, the bracket 600 comprises the cable guide 605, which comprises an elongate casing attached at opposing ends to the cable holder 304 adjacent the humidification apparatus 501 and the lower base member 102 towards a rear end thereof. The casing of the cable guide 605 at least partially engages a power cable (not shown) of the humidification apparatus 501 over substantially the entire length of the power cable between the humidification apparatus 501 and the lower base member 102. In some embodiments, a power cable may be received and retained by a plurality of discrete, substantially annular projections 604 which at least partially enclose and retain the power cable. That is, the casing of the cable guide 605 has a substantially arcuate or semi-circular cross-section along substantially its entire length, with the plurality of discrete, substantially annular (or partly annular) projections 604 spaced along the casing of the cable guide 605.

In some embodiments, the plurality of projections 604 may be formed by a plurality of fingers that are resiliently separable to receive a power cable. The cable guide 605 deforms with a power cable as the bracket 600 is extended and ensures that there is provided sufficient excess of the power cable to allow full extension of the bracket 600. The elongate casing thus preferably has a length greater than the travel distance of the bracket 600. In some embodiments, the casing of the cable guide 605 may be substantially resilient to guide deformation of a power cable, keeping the power cable away from the sliding mechanism as the humidification apparatus 501 is repeatedly extended and retracted, as shown in FIG. 6. In some embodiments, the cable guide 605 is formed with an internal diameter of 7 mm and an external diameter of 8 mm, but other suitable dimensions may be used. In some embodiments, the cable guide 605 may comprise one or more rubber grommets having a central aperture with a slot extending radially therefrom to the perimeter, through which a power cable may be forcefully inserted and retained thereby.

Also shown in FIG. 6 is a pair of screws 602, 603 threaded through apertures in the jaw 303. In some embodiments, the pair of screws 602, 603 may be rotated in opposing directions, causing axial movement of each of the screws 602, 603 to respectively engage or release a portion of the support structure received between the lower base member 102 and the jaw 303. A clamp pad 606 is provided at a distal end of the screw 602 to increase the contact surface area, increasing friction and preventing damage to the support structure.

Figure 7:
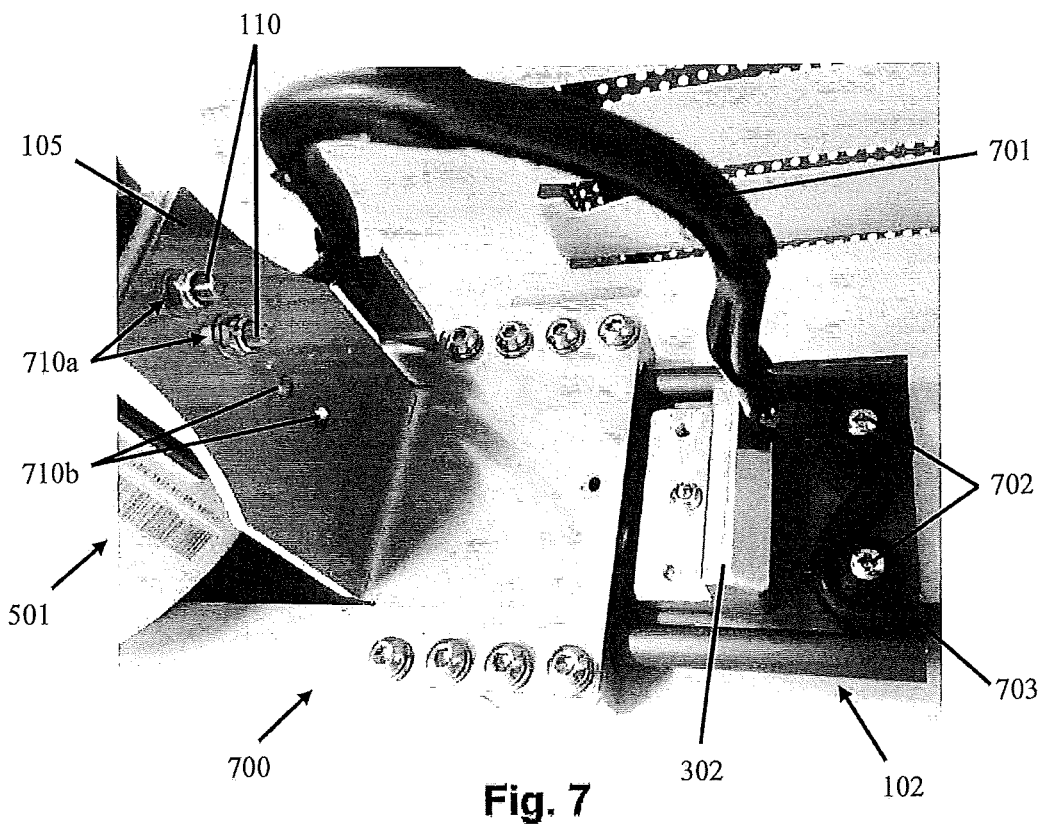
FIG. 7 shows a rear view of a bracket according to an embodiment of the present disclosure and in a retracted position.

FIG. 7 shows a rear view of a bracket 700 according to an embodiment of the present disclosure and in a retracted position. The bracket 700 comprises an alternative embodiment of the cable guide 605 comprising a resilient elongate casing 701 attached at opposing ends to the upright support member 105 and a rear end of the lower base member 102 and a pair of guide posts 702 at a rear end of the lower base member 102 behind the back stopper 302. The resilient elongate casing 701 partially encloses a power cable 703 over substantially the entire length of the resilient elongate casing 701 and ensures that there is provided sufficient excess of the power cable 703 to allow full extension of the bracket 700, The casing is preferably substantially resilient to guide deformation of the power cable away from the sliding mechanism as the humidification apparatus 501 is repeatedly extended and retracted. The power cable 703 is then wrapped partially about each of the pair of guide posts 702 in, for example, an S-shape, to secure the cable and prevent movement thereof as the bracket 700 is repeatedly extended and retracted, and to prevent unintentional disengagement of the power cable 703 during service of the support structure.

In some embodiments, the bolts 110 secure the channel 106 (not shown in FIG. 7) to the upright support member 105 and are inserted through apertures 710a (obscured) in the upright support member 105. In some embodiments, additional apertures 710b in the upright support member 105 provide an alternative attachment position for the channel 106 relative to the upright support member 105, whereby the channel 106 may be attached to a higher attachment position of the upright support member 105 using the apertures 710a or to a lower attachment position of the upright support member 105 using the apertures 710b. In some embodiments, the higher and lower attachment positions provided by the apertures 710a, 710b may be suitable for use with different types or sizes of the humidification apparatus 501 or other medical or surgical apparatus.

The humidification apparatus 501 shown in FIGS. 5-7 is the HumiGard™ system available from Fisher & Paykel Healthcare Ltd. of Auckland, New Zealand, although it will be appreciated that the apparatus and systems disclosed herein are not limited to use with this model and may be suitably modified if necessary to work with any other medical/surgical apparatus without departing from the intended scope of this disclosure.

As shown in FIG. 5, the humidification chamber of the humidification apparatus 501 in use may sit atop the heater plate on top of the apparatus. Conduits (not shown) may in turn be coupled to the inlet and outlet at the top of the humidification chamber. Such removable components of the humidification apparatus 501 may contribute to the overall height of the apparatus. Fixed mounting of the humidification apparatus 501 within an enclosed space according to the prior art, such as on a shelf of a support structure, may thus dictate the separation of the shelving and the proximity of a neighboring shelf provided immediately above the humidification apparatus 501. When attached to a bracket such as one of those disclosed herein, however, the humidification apparatus 501 may be extended beyond such shelving prior to installation of the humidification chamber and conduits, enabling denser shelving and greater storage in the support structure. These components can be removed when the humidification apparatus 501 is no longer required, and the humidification apparatus 501 can be again retracted inside the support structure, out of the way.

Figure 8:
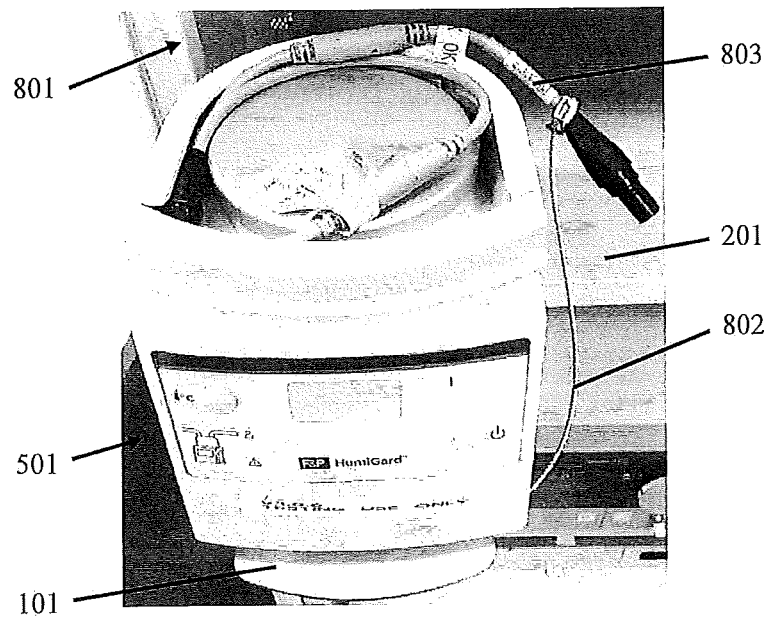
FIG. 8 shows a front view of a humidification apparatus attached to the bracket of FIG. 1 and with the addition of a lanyard.

FIG. 8 shows a front view of the humidification apparatus 501 attached to the mounting member 101 of the bracket 100 (obscured) according to an embodiment of the present disclosure and in the fully extended position, projecting from the shelf 201 of a support structure 801 (shown only in part). Also shown is a lanyard 802 which may be used to retain a sensor cable 803 of the humidification apparatus 501, for example. The lanyard 802 is attached at opposing ends to the bracket 100 and the sensor cable 803 to prevent loss, theft, or inadvertent disposal of the reusable sensor cable 803 with a disposable conduit, for example. The lanyard 802 may comprise a multi-strand steel wire rope, for example.

Figure 9:
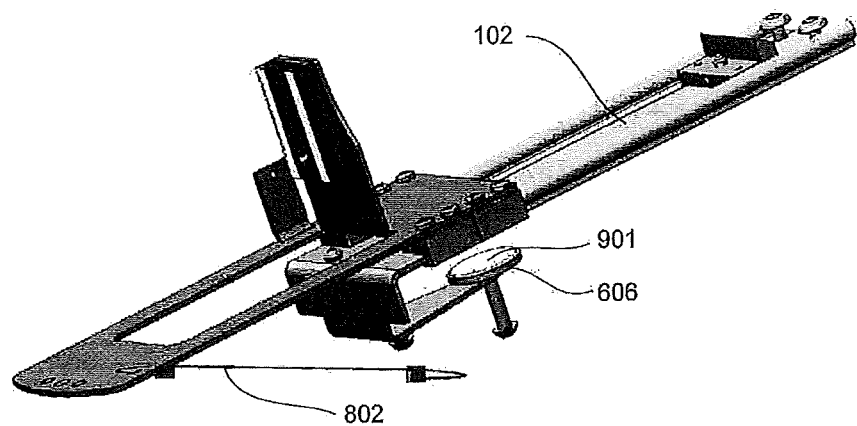
FIG. 9 shows an isometric view of a bracket according to an embodiment of the present disclosure and in an extended position.
Figure 10:
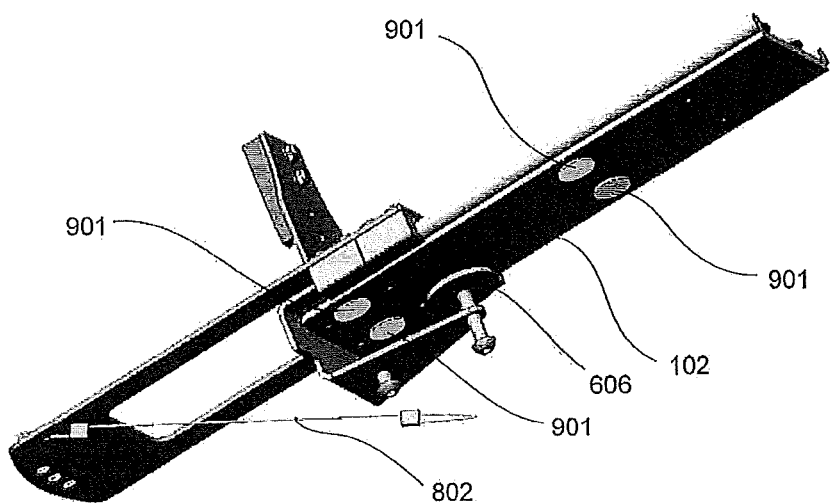
FIG. 10 shows an alternative isometric view of the bracket of FIG. 9.

FIGS. 9 and 10 show isometric views of a bracket 900 according to an embodiment of the present disclosure and in a fully extended position. In FIGS. 9 and 10, a plurality of gripping feet 901 are attached to a lower surface of the lower base member 102 and a facing surface of the clamp pad 606, between which a shelf is received in use. The gripping feet 901 may comprise a rubber or elastomer material may which improves the stability of the bracket 900 by increasing the friction with the mounting surface. The gripping feet 901 may be adhered to the bracket 900.

Figure 11A:
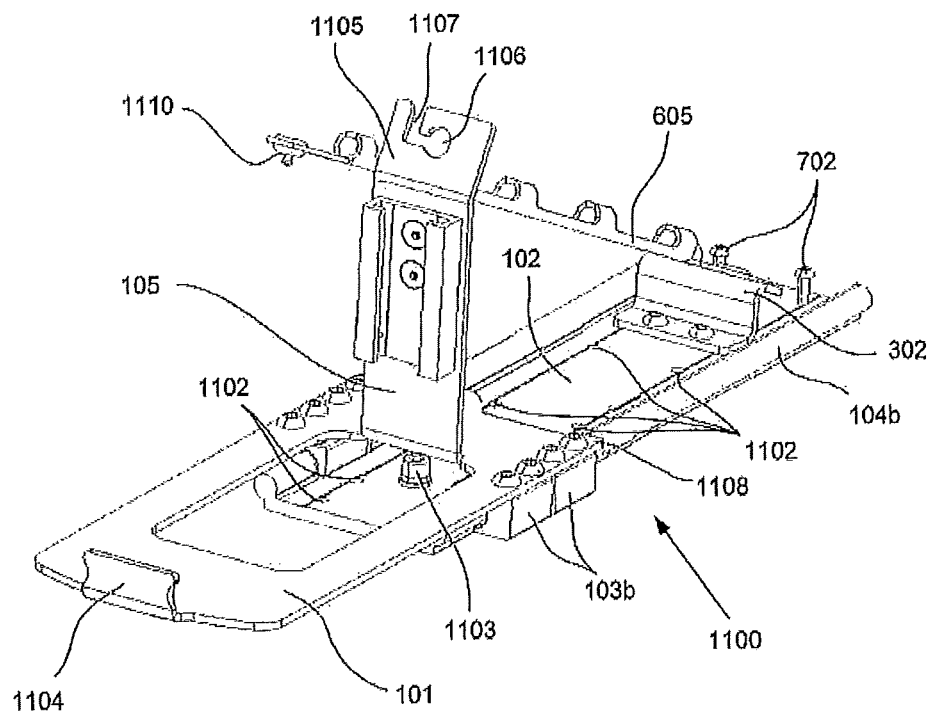
FIG. 11a shows a front isometric view, and FIG. 11b a rear isometric view, of a bracket according to an embodiment of the present disclosure.
Figure 11B:
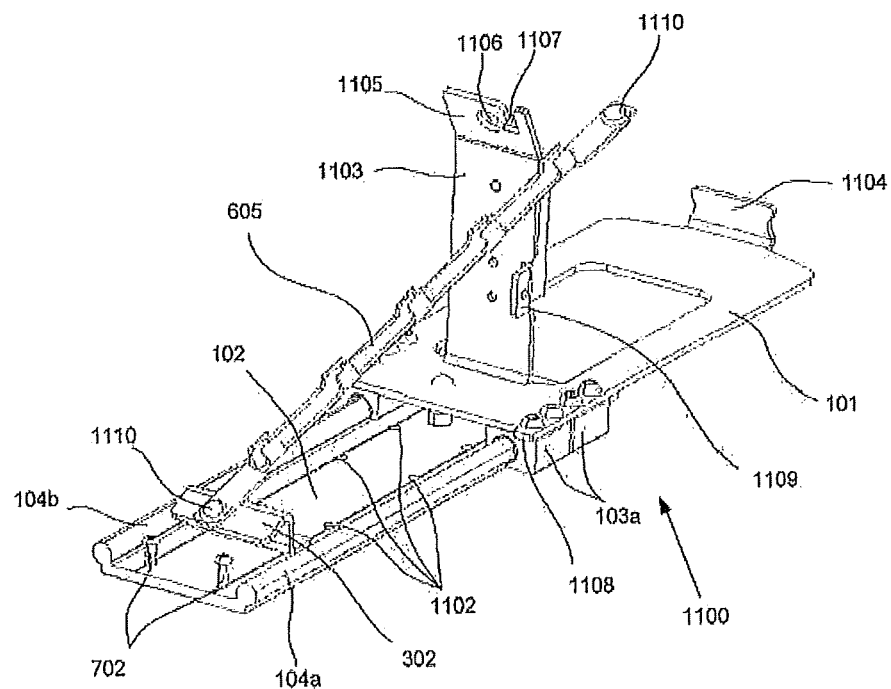

FIGS. 11a and 11b show views of a bracket 1100 according to an embodiment of the present disclosure. The bracket 1100 of this embodiment is largely similar to those of the above-described embodiments. For convenience, only the differences are described in detail below. Some reference numerals are omitted from the drawings for clarity.

Due to differences in the design of various support structures to which a humidification apparatus may be secured, the clamp of the foregoing embodiments may not always be suitable. For example, a lip or handle at a front of a shelf may impede secure or level attachment of the bracket 1100 to the shelf and/or obstruct extension of the mounting member 101. Alternatively, upper surfaces of shelves may be fully occupied or required for other purposes. In some cases, therefore, it may be preferable to mount the humidifier to an internal surface of a side wall of a support structure, an external surface of the side wall, or a downward-facing surface of a top wall or shelf, rather than necessarily atop a horizontal surface such a shelf, top wall, or bottom wall of the support structure.

Figure 12:
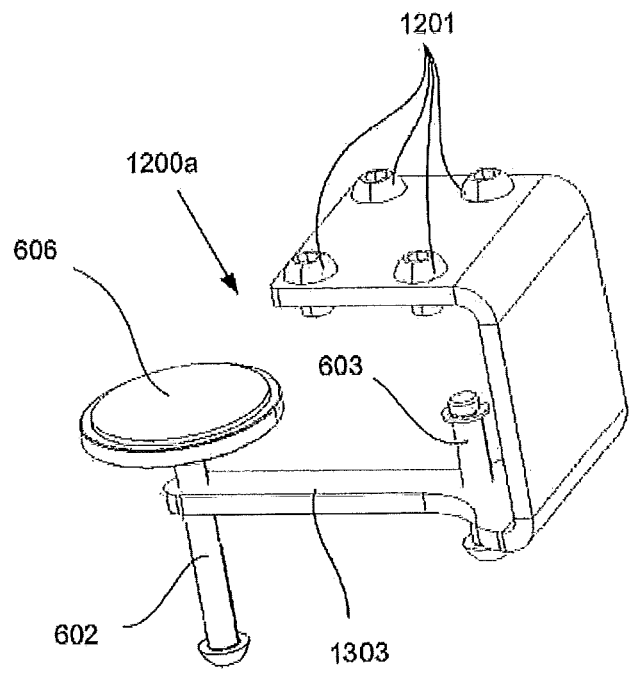
FIGS. 12a and 12b show isometric views of mounting adapters for use with the bracket of FIGS. 11a and 11b, according to embodiments of the present disclosure.
Figure 12:
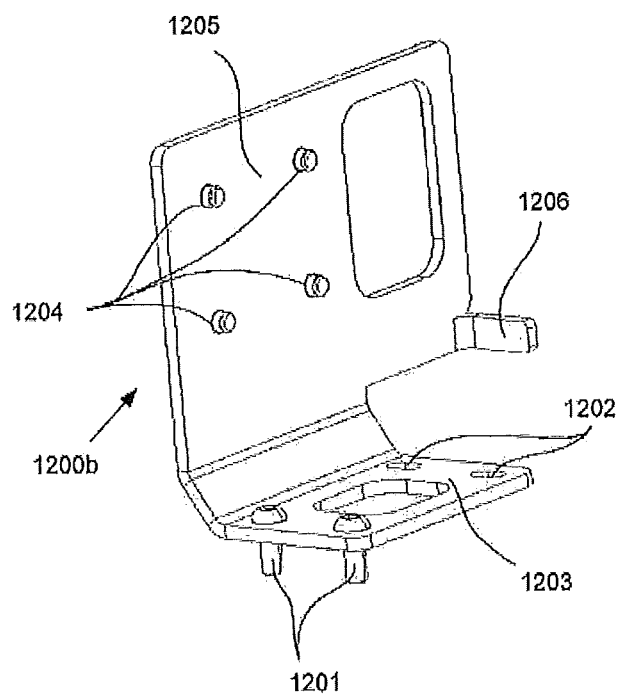

According to the present embodiment, the lower base member 102 of the bracket 1100 is adapted to engage with a plurality of modular mounting adapters, each differing in at least one aspect, to provide flexibility in mounting of the bracket 1100 to a support structure. Two examples of such mounting adapters are shown in FIGS. 12a and 12b, respectively, and are described in further detail below, but a variety of other mounting adapters may alternatively be used without departing from the scope of the disclosure.

The bracket 1100 is shown in generalized FIG. 11 without a mounting adapter attached. A suitable mounting member may be selected and attached by way of a plurality of fasteners, for example but not limited to a plurality of bolts 1201 (shown in generalized FIG. 12), inserted through two or more of a plurality of mounting holes 1102 (some of which are obscured in the drawing) provided in the lower base member 102 and corresponding mounting holes 1202 (shown in generalized FIG. 12) in the mounting adapters. In some embodiments, the lower base member 102 may comprise one or more of the plurality of mounting holes 1102 in various positions which may not initially be used by existing mounting adapters, to allow for use with future mounting adapters designed for use with new support structures as they are released, for example.

The front stopper 301 in this embodiment is replaced by a stopper bolt 1103 which projects upwardly from the lower base member 102 to engage a corresponding projection or bolt (obscured) projecting downwardly from the mounting member 101. The carriages 103a, 103b thus do not directly engage either of the stoppers 301, 302, enabling greater travel or extension of the mounting member 101 and also protecting bearings of the carriages 103a, 103b.

A handle 1104 is provided at a forward end of the mounting member 101 to facilitate extension and retraction of the mounting member 101 and the humidification apparatus mounted thereon. In some embodiments, the handle 1104 projects upward to avoid pinching the user's fingers between the handle 1104 and a shelf of a support structure upon retracting the mounting member 101. In some embodiments, the handle 1104 may project downward.

Referring still to the embodiment of generalized FIG. 11, the bracket 1100 comprises an alternative embodiment of the upright support member 105 with a backwardly-angled top portion 1105. The top portion 1105 comprises a cable aperture 1106 and a cable slot 1107 extending from the cable aperture 1106 to an outer edge of the top portion 1105 and replaces the cable holder 304 of the preceding embodiments. As shown in the drawings, both the top portion 1105 and the upright support member 105 may be formed from the same sheet metal as the lower base member 102, accounting for the void shown in the central area of the lower base member 102. The top portion 1105 may therefore be preferred over the cable holder 304 for manufacturability and/or cost reduction.

In use, a power cable of the humidification apparatus may be passed through the cable slot 1107 to the cable aperture 1106 and retained and guided thereby towards the cable guide 605. In some embodiments, the cable slot 1107 may comprise a right angle or dog-leg to prevent a power cable escaping the cable aperture 1106 inadvertently. In some embodiments, the cable slot 1107 may extend from the cable aperture 1106 radially sideways towards the adjacent end of the cable guide 605, before angling upwards to the top edge of the top portion 1105. In some embodiments, due to the limited resilience and angle of a power cable in extending through the cable aperture 1106 and across towards the cable guide 605, the power cable will generally be urged substantially away from the cable slot 1107. The upright support member 105 of this embodiment is also better suited for use with a variety of different types of humidification apparatus, which may have substantially different dimensions and/or different attachment locations for power cables, for example.

In some embodiments, the cable guide 605 may be adapted to securely retain and guide power cables of various diameters ranging from, for example, 5.0 to 9.0 mm, or more preferably 6.9 to 7.9 mm. More particularly, the cable guide 605 is preferably formed with an internal diameter of approximately 8 mm and an external diameter of approximately 12 mm. Although the cable guide 605 of the bracket 1100 is shown in a substantially linear configuration in generalized FIG. 11, it will be observed that it is attached to the bracket 1100 at only one end. In some embodiments, the cable guide 605 may comprise a resilient plastic material attached to the bracket 1100 at or adjacent opposing ends of the cable guide 605 as described below, whereby the cable guide 605 does not interfere with the full extension and retraction of the mounting member 101, whilst urging the power cable away from the bracket 1100 to prevent jamming the bracket 1100 upon retraction of the mounting member 101.

In some embodiments, opposing ends of the cable guide 605 may be attached to a tab 1109 projecting rearwardly from the upright support member 105 and the top of the back stopper 302 towards the rear end of the lower base member 102 of the bracket 1100 by a retainer 1110 inserted through corresponding apertures therein. In particular, the retainer 1110 comprises a shaft of diameter equal to or less than the aperture. In some embodiments, at a proximal end of the shaft, the retainer 1110 may comprise a head of relatively broad diameter (with respect to the shaft and aperture), providing a surface for forcibly engaging the retainer 1110 with the apertures. In some embodiments, at a distal end of the shaft, the retainer may comprise an elastically-deformable flange of a diameter at least in part greater than the aperture, yet compressible to a diameter less than or substantially equal to that of the aperture to facilitate its passage therethrough. The flange is compressed upon forceful insertion through the corresponding apertures, and resiliently expands upon emerging to abut a rear side of the upright support member 105 or the back stopper 302, respectively. In some embodiments, the flange may be bevelled or chamfered to facilitate insertion through the aperture but resist inadvertent removal in the opposing direction. The flange may also pass through and engage a central aperture of a washer (not shown). In some embodiments, the washer may comprise a similar plastic material to the retainer 1110 and may have an outer diameter similar to the head of retainer 1110.

The back stopper 302 of the bracket 1100 may be stamped from sheet metal rather than being machined from aluminium in this embodiment, and may comprise a plurality of apertures for receiving retainer 1110.

FIGS. 12a and 12b show isometric views of two embodiments of mounting adapters according to embodiments of the present disclosure which may be used to secure the lower base member 102 of the bracket 1100 to a support structure.

FIG. 12a shows a mounting adapter comprising a clamp 1200a which may be used to secure the bracket 1100 atop a horizontal shelf, for example. The clamp 1200a may be attached to the forward end of the bracket 1100 by passing each of the bolts 1201 through the corresponding holes 1102, 1202 (obscured in FIG. 12a) in the lower base member 102 and the clamp 1200a, respectively. In some embodiments, the holes 1102 in the lower base member 102 may be threaded to receive and retain the bolts 1201 upon tightening thereof. In some embodiments, the holes 1202 in the clamp 1200a may be not threaded. In some embodiments, the holes 1102 may be unthreaded and the holes 1202 threaded, both of the holes 1102, 1202 may be threaded, and/or a nut may be threaded onto a distal end of each the bolts 1201 to secure the clamp 1200a to the bracket 1100. Either or both of the holes 1102, 1202 may be countersunk or counterbored to receive the heads of the bolts 1201 or a nut, in particular to provide a flat attachment surface on the bottom of the lower base member 102.

As in the embodiment of FIG. 3, the clamp 1200a comprises a jaw 1203 which in use extends downwardly and rearwardly from the forward end of the bracket 1100 to receive a shelf between the jaw 1203 and the lower base member 102. The threaded screws 602, 603 may be turned in either direction to respectively engage or release a shelf between the lower base member 102 and the clamp pad 606 and the distal end of the screw 603, respectively.

Compared to the jaw 303, it can be observed that the rearwardly-extending arm portion of the jaw 1203 is significantly narrower. It has been found that the narrowed portion compensates for bending moment forces, by allowing elastic bending of the jaw 1203 and thereby reducing the chance of plastic deformation of the clamp 1200a.

FIG. 12b shows a mounting adapter comprising a substantially L-shaped side-mounting adapter 1200b for attaching the bracket 1100 to a vertical surface of a support structure, such as an interior or exterior surface of a substantially vertical side wall of an instrument stand, for example. Using the side-mounting adapter 1200b, the humidification apparatus may be mounted above any lip, handle, or other obstruction at the front of a shelf, or at a more convenient height for use, for example.

Side-mounting adapter 1200b is attached to the bracket 1100 by the bolts 1201 passing through the lower base member 102 and the mounting holes 1202 in the bottom plate 1203, and to the support structure by the bolts 1204 passing through mounting holes in a side plate 1205.

A back stopper 1206 projects from the side plate 1205 of the side-mounting adapter 1200b. The back stopper 1206 may, in use, be positioned forward of the back stopper 302 on the lower base member 102 to protect components of the humidification apparatus, such as a probe projecting from a rear of the humidification apparatus. The back stopper 1206 engages one of the pair of projections 1108 on the rear end of the mounting member 101 (see generalized FIG. 11) to limit rearward sliding movement of the mounting member 101, in preference to the back stopper 302 on the lower base member 102. The projections 1108 avoid contact between the carriages 103a, 103b and the back stoppers 302, 1206 to avoid any potential damage to the carriages 103a, 103b and/or bearings of the carriages 103a, 103b.

The clamp 1200a and the side-mounting adapter 1200b are shown and described in detail by way of example only. Other mounting adapters, including at least a mirror image of side-mounting adapter 1200b for mounting to the opposing side of the bracket 1100, may be provided to enable further mounting options. Alternatively, or additionally, yet other mounting adapters may differ in at least in terms of mere dimensions or materials.

The various bolts and screws of the bracket 1100 and mounting adapters may have a common bolt/screw head or socket so that they can all be turned using a single tool such as a #5 hex/Allen key, for example, but any alternative head/socket and/or size may alternatively be used. Such a tool may be provided with the bracket 1100. In some embodiments, those bolts and/or screws which may require adjustment or removal have a commonplace head so that they can be easily adjusted using a readily-available tool such as the aforementioned hex key, while those which are intended as being more permanent or adjustable have one or more different and less-commonplace heads to discourage tampering. By way of non-limiting example, the latter bolt/screw heads may comprise one or more of a Torx, security Torx, Torq-set, or Tri-wing socket. For example, in one embodiment the screws 602, 603 may have a #5 hex socket head, while the bolts 109, 1101, 1201, 1204 may have a security Torx socket head.

Figure 13A:
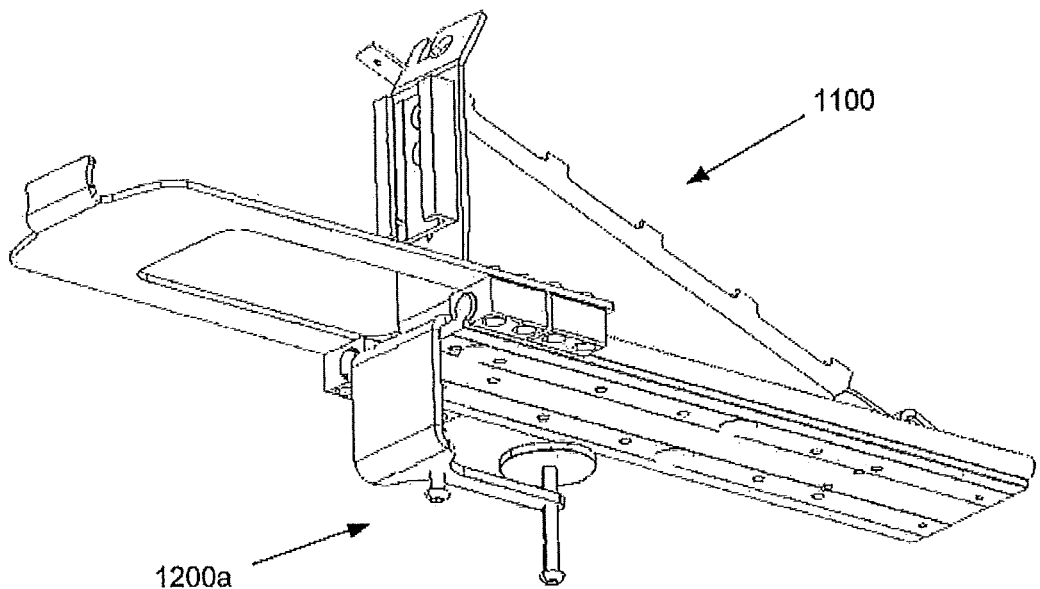
FIGS. 13a and 13b show isometric views of the bracket of FIGS. 11a and 11b attached to each of the the mounting adapters of FIGS. 12a and 12b, respectively.
Figure 13B:
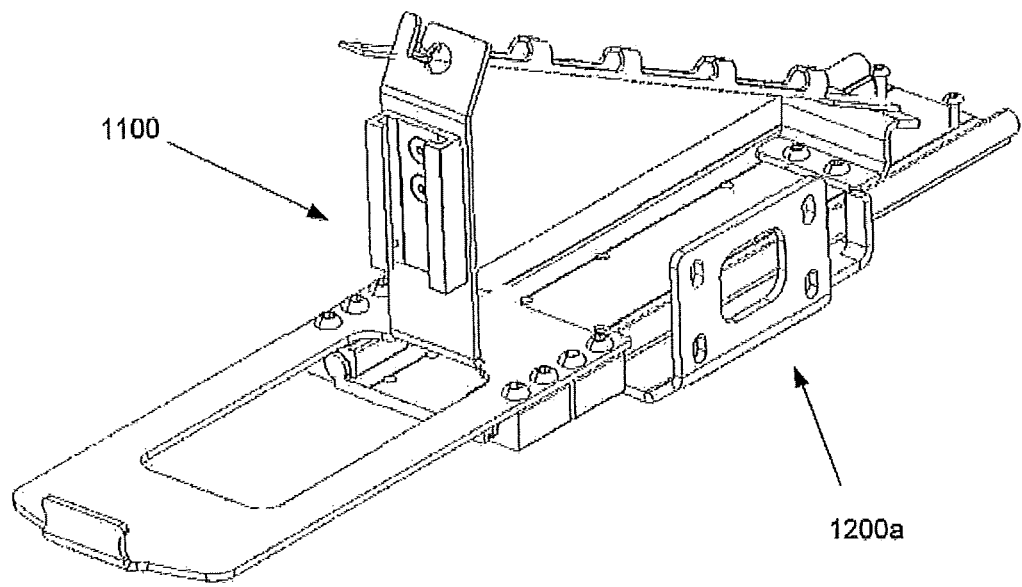

FIG. 13a shows the bracket 1100 attached to the clamp 1200a of FIG. 12a, and FIG. 13b shows the bracket 1100 attached to the side-mounting adapter 1200b of FIG. 12b.

The disclosed apparatus and systems may also be said broadly to consist in the parts, elements and features referred to or indicated in the specification of the application, individually or collectively, in any or all combinations of two or more of said parts, elements or features. Furthermore, where reference has been made to specific components or integers of the disclosed apparatus and systems having known equivalents, then such equivalents are herein incorporated as if individually set forth.

Unless the context clearly requires otherwise, throughout the description, the words "comprise", "comprising", and the like, are to be construed in an inclusive sense. That is to say, in the sense of "including, but not limited to", as opposed to an exclusive or exhaustive sense.

Any discussion of the prior art throughout the specification should in no way be considered as an admission that such prior art is widely known or forms part of common general knowledge in the field.

Although the disclosed apparatus and systems have been described by way of example and with reference to possible embodiments thereof, it is to be understood that modifications or improvements may be made thereto without departing from the scope of the disclosed apparatus and systems. For example, whilst the above-described linear sliding or carriage mechanism may be preferred for stability and reliability reasons, in alternative embodiments the sliding mechanism may comprise a single rail, or the extension mechanism may comprise a telescopic extension mechanism comprising a plurality of elongate co-axial telescoping members, or a pantograph mechanism comprising a plurality of articulated linkage members. Furthermore, while the movement of the bracket in the preferred embodiments may be strictly linear, the disclosed apparatus and systems are not limited thereto. The mounting member may also swivel or rotate with respect to the lower base member, for example. Furthermore, while movement of the bracket is preferably manually actuated, the bracket may alternatively comprise an electric, pneumatic, or hydraulic linear actuator to extend and retract the apparatus on demand. In yet other embodiments, the clamp securing the bracket to a support structure may comprise a spring clamp, speed clamp, or any other suitable type of clamp.

From the foregoing it will be seen that a bracket has been disclosed which conveniently enables a moveable mounting of a humidification apparatus to an existing support structure to overcome the disadvantages of merely placing or permanently affixing the apparatus on the support structure. In preferred embodiments the humidification apparatus may be easily retracted within a tower for convenient storage and protection from theft or damage, and extended from the tower to provide easy access for configuration and use. Removable components can be installed on the apparatus after extension, and removed from the apparatus prior to retraction to minimise space requirements within the tower and maximise storage therein. In at least some embodiments, the bracket may be secured to a wide range of existing and/or future support structures using one of a plurality of mounting adapters engageable with the base of the bracket.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A bracket for extensibly mounting a medical apparatus to a support structure, the bracket comprising:
   a base member securable to the support structure;
   a mounting member to which the medical apparatus may be secured; and
   an extension mechanism moveably engaging the base member and the mounting member; and
   a cable guide configured to receive a power cable of the medical apparatus and direct the power cable away from the extension mechanism, the cable guide comprising an elongate cable guide attached at opposing ends to the mounting member and the base member and engageable with substantially an entire length of the power cable therebetween, the elongate cable guide adapted to secure a sufficient length of the power cable to allow extension of the bracket and to direct the power cable substantially upwardly away from the bracket to prevent obstruction of the extension mechanism as the mounting member is retracted in use, wherein the mounting member is reversibly extensible from a retracted position substantially proximate the base member to an extended position projecting beyond the base member.

2. The bracket of claim 1, wherein the mounting member is slidable with respect to the base member.

3. The bracket of claim 1, wherein the extension mechanism comprises a pair of rails and a pair of carriages slidably engaged with the pair of rails.

4. The bracket of claim 3, wherein the pair of rails are attached to or integral with the base member, the pair of carriages are attached to or integral with the mounting member at or adjacent a rearward end of the mounting member, and a forward end of the mounting member projects beyond the base member in the extended position.

5. The bracket of claim 3, wherein each one of the pair of carriages comprises a channel slidably receiving and retaining a respective one of the pair of rails.

6. The bracket of claim 3, wherein the pair of rails extend linearly from, at, or adjacent a rearward end of the base member to, at, or adjacent a forward end of the base member.

7. The bracket of claim 1, wherein the cable guide comprises an annular cable guide on each of the mounting member and the base member, the annular cable guides adapted to direct the power cable substantially upwardly away from the bracket to prevent obstruction of the extension mechanism as the mounting member is retracted in use.

8. The bracket of claim 1, comprising a front stopper to limit movement of the mounting member in a first direction past the extended position.

9. The bracket of claim 1, comprising a back stopper to limit movement of the mounting member in a second direction past the retracted position.

10. The bracket of claim 1, comprising a lanyard attached at one end to the bracket and attachable at the other end to a cable of the medical apparatus to prevent loss of the cable.

11. The bracket of claim 1, wherein the cable guide comprises a plurality of discrete, substantially annular or partly annular projections configured to receive and retain the power cable.

12. The bracket of claim 11, wherein a casing of the cable guide has a substantially arcuate or semi-circular cross-section along substantially its entire length, with the plurality of discrete, substantially annular or partly annular projections spaced along the casing of the cable guide.

13. The bracket of claim 1, wherein a casing of the cable guide is substantially resilient to guide deformation of the power cable.

14. A bracket for slidably mounting a medical apparatus to a support structure, the bracket comprising:
a base plate comprising a first side engageable and securable to the support structure and an opposing second side comprising a pair of rails;
a mounting plate comprising a first side comprising a pair of carriages slidably engaging the pair of rails and a second side adapted to support the medical apparatus; and
a cable guide configured to receive a power cable of the medical apparatus and direct the power cable away from the extension mechanism, the cable guide comprising an elongate cable guide attached at opposing ends to the mounting plate and the base plate and engageable with substantially an entire length of the power cable therebetween, the elongate cable guide adapted to secure a sufficient length of the power cable to allow extension of the bracket and to direct the power cable substantially upwardly away from the bracket to prevent obstruction of the mounting plate as the mounting plate is retracted in use,
wherein the mounting plate is slidable in opposing linear directions along the rails to linearly extend and retract the medical apparatus with respect to the base plate and the support structure.

15. The bracket of claim 14, wherein the pair of rails extends linearly from, at, or adjacent a rearward end of the base plate to, at, or adjacent a forward end of the base plate.

16. The bracket of claim 14, wherein the cable guide comprises an annular cable guide on each of the mounting plate and base plate, the annular cable guides adapted to direct the power cable substantially upwardly away from the bracket to prevent obstruction of the mounting plate as the mounting plate is retracted in use.

17. The bracket of claim 14, comprising a lanyard attached at one end to the bracket and attachable at the other end to a cable of the medical apparatus to prevent loss of the cable.

* * * * *